United States Patent [19]

von Bittera

[11] Patent Number: 4,738,670
[45] Date of Patent: Apr. 19, 1988

[54] MEDICINAL PLASTERS

[75] Inventor: Miklos von Bittera, Leverkusen, Fed. Rep. of Germany

[73] Assignee: Bayer Aktiengesellschaft, Leverkusen, Fed. Rep. of Germany

[21] Appl. No.: 72,063

[22] Filed: Jul. 10, 1987

Related U.S. Application Data

[63] Continuation of Ser. No. 709,970, Mar. 11, 1985, abandoned.

[30] Foreign Application Priority Data

Mar. 13, 1984 [DE] Fed. Rep. of Germany ........ 3409079

[51] Int. Cl.$^4$ .................................................. A61L 15/06
[52] U.S. Cl. ........................................ 604/306; 424/447
[58] Field of Search ................ 604/304, 307, 896–897; 424/19, 22; 128/156

[56] References Cited

U.S. PATENT DOCUMENTS

| | | | |
|---|---|---|---|
| 3,742,951 | 7/1973 | Zaffaroni | 604/304 |
| 3,797,494 | 3/1974 | Zaffaroni | 604/897 |
| 3,964,482 | 6/1976 | Gerstel et al. | 604/896 |
| 4,031,894 | 6/1977 | Urquhart et al. | 604/897 |
| 4,060,084 | 11/1977 | Chandraseharan | 604/897 |
| 4,201,211 | 5/1980 | Chandraseharan | 604/897 |
| 4,215,684 | 8/1980 | Wertip | 128/156 |
| 4,236,550 | 12/1980 | Braun et al. | 128/156 |
| 4,314,557 | 2/1982 | Chandraseharan | 604/307 |
| 4,435,180 | 3/1984 | Leeper | 604/896 |
| 4,476,697 | 10/1984 | Schafer et al. | 128/156 |
| 4,486,788 | 12/1984 | Pietsch et al. | 128/156 |
| 4,542,739 | 9/1985 | Schafer et al. | 128/156 |
| 4,559,222 | 12/1985 | Enscore et al. | 424/22 |
| 4,573,996 | 3/1986 | Kwiatek et al. | 604/897 |

FOREIGN PATENT DOCUMENTS

| | | |
|---|---|---|
| 1667940 | 5/1972 | Fed. Rep. of Germany . |
| 2045593 | 3/1971 | France . |
| 2497457 | 7/1982 | France . |
| 2527450 | 12/1983 | France . |
| 82/00099 | 1/1982 | PCT Int'l Appl. . |
| 2073588 | 10/1981 | United Kingdom . |

OTHER PUBLICATIONS

Billmeyer, *Textbook of Polymer Science*, 3rd Ed. Wiley & Sons, N.Y., 1984, p. 529.
Patents Abstracts of Japan, Band 7, Nr. 155 (C-175) [1300], 7, Jul. 1983, Tokyo, JP: & JP-A 5867 617 (Nitto Denki Kogyo K.K.) 22.04.1983.

*Primary Examiner*—C. Fred Rosenbaum
*Assistant Examiner*—Mark Colosimo
*Attorney, Agent, or Firm*—Sprung Horn Kramer & Woods

[57] ABSTRACT

A medicinal plaster comprising a covering layer, a reservoir layer for an active compound and a detachable protective layer is disclosed. The covering is a substantially impermeable material comprising a textile sheet-like structure which is longitudinally and transversely elastic and is impregnated or coated with a polymer. Disposed on such a covering layer is a reservoir layer comprising 1 to 30% by weight of active compound is an elastomeric mixture comprising a polyisobutylene polymer, a carrier such as a polybutadiene oil or liquid paraffin and a resin such as a polybutadiene oil or liquid paraffin and a resin such as a adhesion-conferring resin. Methods for the formation of such medicinal plaster and the use of such medicinal plaster, especially to apply large dosages of antiinflammatory materials are disclosed.

22 Claims, No Drawings

MEDICINAL PLASTERS

This is a continuation of application Ser. No. 709,970, filed Mar. 11, 1985, now abandoned.

The invention relates to medicinal plasters for the release of an active compound on the skin over a prolonged period, in particular to antiinflammatory medicinal plasters, whose covering layer comprises a textile sheet-like structure, in particular simultaneous or consecutive course formation knit, which is longitudinally and transversely elastic and is impregnated or coated with a polymer.

Medicinal plasters which have a reservoir of mineral oil and polyisobutene are described in U.S. Pat. No. 4,031,894. The polyisobutene is a mixture of components of various molecular weights, namely PIB of M.W. 35,000-50,000 and 1,000,000-1,500,000.

This plaster is suitable only for active compounds which need to be administered in very low doses. Scopolamine is mentioned.

Thus, an object of the present invention is to provide medicinal plasters whereby it is possible to administer through the skin controlled, relatively large, therapeutically effective amounts of an active compound over a prolonged period. These plasters are intended to be particularly suitable for administration of antiinflammatory agents. They are intended to be tolerated by the skin. Hence, one can administer high therapeutically effective doses of the active compound.

Known systems for releasing active compounds, such as, for example, gels, ointments, plasters and the like, permit only limited absorption of active compound through the skin. The absorption depends on the base and the properties of the active compound.

The invention relates to medicinal plasters for the administration of an active compound through the skin, containing a covering layer comprising a textile sheet-like structure, in particular simultaneous or consecutive course formation knit, which is longitudinally and transversely elastic and impregnated or coated with a polymer, a reservoir layer and a detachable protective layer, the reservoir layer containing a polymer comprising polyisobutylene and/or its copolymers, a carrier and a resin. Polymers within the meaning of the present invention are to be understood to be polyisobutylene and/or its copolymers.

Polyisobutylenes within the meaning of the invention are to be understood to be polyisobutylenes which, depending on the preparation, have a molecular mass distribution $M_w/M_n$ of 1.5 to 3.5, preferably 2.0 to 3.0, and a viscosity average of molecular mass—again depending on preparation—of 30,000 to 4,000,000 g/mol. The viscosity average of the polyisobutylenes to be used according to the invention is preferably 50,000 to 1,000,000 g/mol, particularly preferably 80,000 to 500,000 g/mol. The viscosity averages can be determined in a known manner in accordance with Polymer Handbook, J. Brandrup and F. H. Immergut, Wiley & Sons, New York, 1975, Chapter IV, page 35.

These polyisobutylenes have been known for a long time and can be prepared using acid catalysts in accordance with, for example U.S. Pat. No. 2,203,873 or German Pat. No. 704,038.

Copolymers of isobutylene in the meaning of the invention are those of isobutylene having 0.5-5 mol-% of conjugated diolefins preferably those having 4-6 C atoms, such as, for example, 1,3-butadiene, piperylene and 2,3-dimethylbutadiene, particularly preferably with isoprene, whose molecular masses can range from 30,000 to 200,000 g/mol. These isobutene copolymers are also known. Polyisobutylene homopolymers having a viscosity average of 80,000 to 500,000 are very particularly preferably used.

Carriers within the meaning of the present invention are to be understood to be oils, fatty acid esters, triglycerides, alcohols and/or fatty acids.

Oils within the meaning of the present invention are to be understood to be high-boiling, aliphatic, araliphatic and/or aromatic hydrocarbons, preferably liquid paraffin, Purcellin oil, perhydrosqualene and solutions of microcrystalline waxes in the oils, mineral oils, preferably oils whose boiling range is between 150° C. and 400° C., also unsaturated hydrocarbons having at least 16 C atoms, such as, for example, oligomers of monoolefines, such as tetraisobutylene, pentaisobutylene, hexaisobutylene or liquid polymers comprising diene(-monoene) (co)polymers. Examples of liquid polymers of conjugated dienes are those of butadiene, isoprene, 1,3-pentadiene, 2,3-dimethylbutadiene, copolymers of various dienes, as well as liquid copolymers of a conjugated diolefin and small amounts of monoolefins, such as, for example, 1-butene, isobutene, 1-hexene, 1-octene and styrene having MW from 400 to 6,000, preferably 800 to 3,000, and iodine numbers from 200 to 500, and viscosities of 100-10,000 cP at 50° C.

Liquid polybutadiene polymers which are at least 90% 1,4-linked, whose proportion of cis double bonds is more than 60%, and whose molecular masses are 1,000-4,000, are particularly preferred.

Oils are also to be understood to be silicone oils of various viscosities, preferably having mean molecular weights of 312 to 15,000, particularly preferably polydimethylsiloxanes.

The fatty acid esters are to be understood to be those which contain at least 12 C atoms, preferably 15 to 46 C atoms, particularly preferably 16 to 36 C atoms. The following are to be understood in particular: ethyl stearate, hexyl laurate, dipropylene glycol pelargonate, cetyl palmitate, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, synthetic duck preen gland fat, in each case singly or in mixtures.

Triglycerides are to be understood to be pure or mixed esters of glycerol with fatty acids of chain length $C_8$-$C_{18}$, preferably triglycerides of caprylic and/or capric acid.

Fatty acids are to be understood to be saturated or unsaturated fatty acids, preferably those having 12-24 C atoms, singly or mixed with one another, particularly preferably oleic acid.

Furthermore, oils within the meaning of the invention are to be understood to be: sweet almond oil, avocado oil, sesame oil, castor oil, olive oil, grapeseed oil, clove oil, arachis oil, maize oil, hazelnut oil, jojoba oil, safflower oil and wheatgerm oil, in each case singly or in mixtures.

Resins within the meaning of the present invention are to be understood to be colophony, dehydrogenated colophony, glycerol esters of dehydrogenated colophony, glycerol esters of colophony gum, hydrogenated colophony, glycerol esters of hydrogenated colophony, pentaerythritol esters of hydrogenated colophony, methyl esters of hydrogenated colophony, polymerized colophony, glycerol esters of polymerized colophony, terpene resins, coumarone/indene resins, hydrogenated petroleum resins, colophony derivatives and colophony modified with maleic anhydride, $C_5$ petroleum resins and hemiesters of styrene/maleic acid copolymers, singly or mixed with one another. Polyterpene resins from alpha- or beta-pinene or modified glycerol esters of colophony are particularly preferred. Depending on the properties required in respect of adhesiveness and strength of adhesion to the part onto which the resulting plaster is intended to be applied, these resins can be used either alone or combined with one another.

Antiinflammatory agents within the meaning of the present invention are one or more antiinflammatory agents of the general formula I and/or II.

Antiinflammatory agents of the general formula I have the following structure:

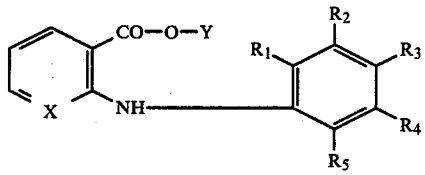

where
R$_1$–R$_5$ can be identical or different, and denote hydrogen, halogen, lower alkyl or substituted alkyl,
X denotes N or CH, and
Y denotes hydrogen, metal ions, alkyl or substituted alkyl.

Halogen denotes fluorine, chlorine or bromine, preferably chlorine and/or bromine, particularly preferably chlorine. Lower alkyl is preferably alkyl having 1–6 C atoms, particularly preferably 1–4 C atoms, and substituted alkyl for R$_1$–R$_5$ preferably denotes trihalogenoalkyl, particularly preferably trifluoromethyl. Metal ions are to be understood to be the ions of alkali metals, alkaline earth metals and of aluminum, preferably sodium. Substituted alkyl for Y preferably denotes alkoxy, alkoxyalkyl, hydroxyalkyl, hydroxyalkoxyalkyl or trihalogenoalkyl, where the number of C atoms is 1 to 6 and the alkyl chain can be straight or branched.

The preferred antiinflammatory agents of the general formula I which are used are those in which
R$_3$ and R$_4$ denote hydrogen,
X denotes nitrogen or a CH group,
Y denotes hydrogen, C$_1$–C$_4$-alkyl or substituted C$_1$–C$_4$-alkyl hydroxyalkyl or hydroxyalkoxyalkyl having 1 to 6 C atoms, and
R$_1$, R$_2$ and R$_5$ denote hydrogen, chlorine, C$_1$–C$_4$-alkyl or trifluoromethyl.

Particularly preferred antiinflammatory agents are those of the general formula I in which
X represents a CH group, and
Y denotes hydrogen or hydroxyalkoxyalkyl having 1 to 6 C atoms, and
R$_1$, R$_2$ and R$_5$ denote methyl, hydrogen, trifluoromethyl or chlorine.

The following antiinflammatory agents are very particularly preferred:

N—(α,α,α-Trifluoro-m-tolyl)anthranilic acid = flufenamic acid

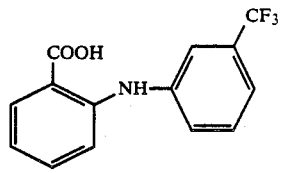

N—(2,3-Xylyl)-anthranilic acid

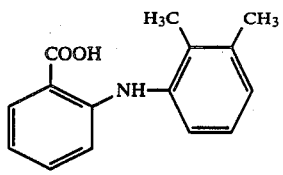

2-(2,6-Xylidino)-nicotinic acid

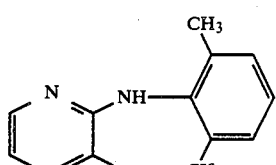

2-(2-Hydroxy-ethoxy)ethyl N—(α,α,α-trifluoro-m-tolyl)anthranilate = etofenamate

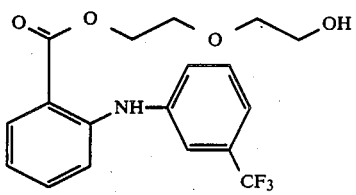

Furthermore, antiinflammatory agents within the meaning of the present invention are antiinflammatory agents of the general formula II, having the structure:

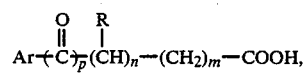

in which
R denotes hydrogen, lower alkyl or substituted alkyl,
Ar denotes aryl, heteroaryl, substituted aryl or substituted heteroaryl, and
n+m denotes an integer and has the value zero, 1 or 2, and
p denotes zero or 1,
with the proviso that Ar does not denote aryl or heteroaryl when n and m and p have the value zero, and their esters or amides.

R for lower alkyl preferably denotes radicals having 1–6 C atoms, preferably 1–4 C atoms, substituted alkyl, alkoxyalkyl or trihalogenoalkyl; aryl or heteroaryl, phenyl, naphthyl, thiophenyl, pyrrolyl, indenyl, indolyl, benzothiazinyl or phenothiazinyl.

Substituents for aryl or heteroaryl are alkyl, preferably straight-chain and branched alkyl having up to 6 C atoms, alkoxy, oxalkyl, acyl, hydroxyl, acetoxy, benzoyl, substituted benzoyl, phenyl, substituted phenyl, phenoxy, halogen, phenylalkenyl or phenylalkyl.

The esters are alkyl esters having 1–6 C atoms, preferably 1–4 C atoms in the alcohol component, particularly preferably methyl, ethyl, i- and n-propyl, substituted alkyl, for example β-hydroxyethyl, esters with glycolic acid. The amides can also contain in the group —CO—NH$_2$ lower alkyls or substituted alkyls in place of one or both amide hydrogens.

The following antiinflammatory agents of the general formula II are particularly preferred:

2-Hydroxy-benzoic acid
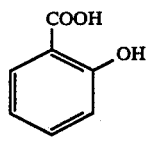

2-Acetoxy-benzoic acid
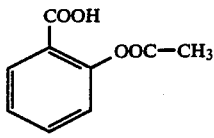

2',4'-Difluoro-4-hydroxy-3-biphenylcarboxylic acid
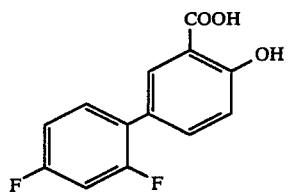

2-Hydroxy-benzamide
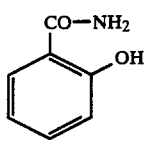

[2-(Amino-carbonyl)-phenoxy]-acetic acid
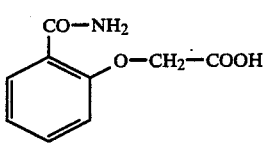

4-Allyloxy-3-chlorophenyl-acetic acid = alclofenac
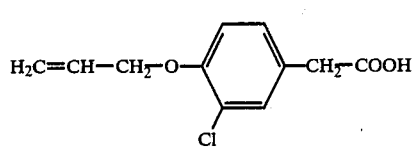

2-[2,6-Di-chlorophenyl)-amino]-phenylacetic acid
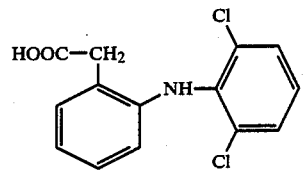

10-Methyl-2-phenothiazinyl-acetic acid = metiazinic acid
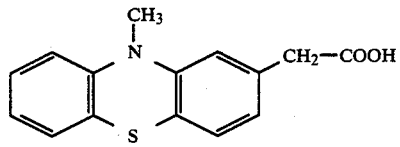

1-Methyl-5-(p-toluoyl)-2-pyrrolyl-acetic acid
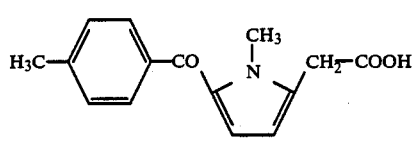

D-2-(6-Methoxy-2-naphthyl)propionic acid = naproxen
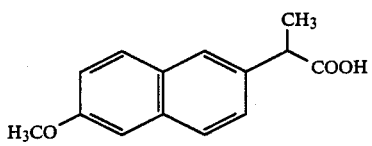

2-(p-Iso-butylphenyl)-propionic acid
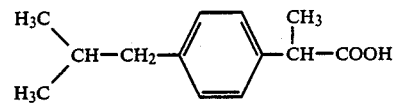

2-(3-Phenoxy-phenyl)-propionic acid
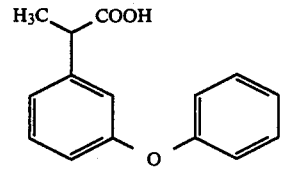

2-(m-Benzoyl-phenyl)pro-pionic acid = ketoprofen
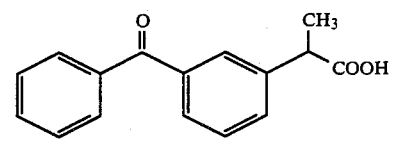

2-[4-(1-Oxo-2-isoindolinyl)-phenyl]propionic acid = indoprofen
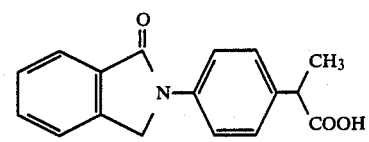

2-(2-Fluoro-4-biphenylyl)-propionic acid
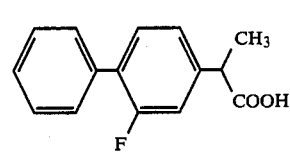

3-(4-Biphenyl-carbonyl)-propionic acid
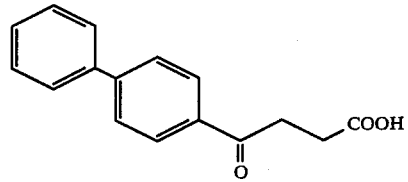

2-(5-Benzoyl-2-thienyl)-propionic acid
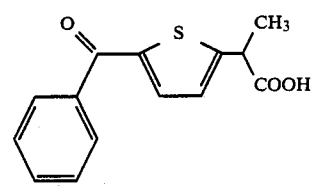

1-(p-Chloro-benzoyl)-5-methoxy-2-methylindole-3-acetic acid = indomethacin
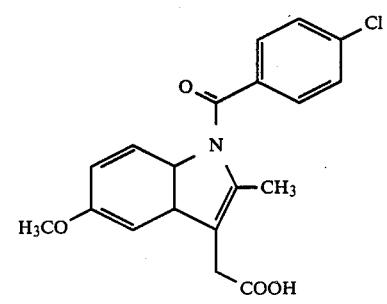

1-(p-Chloro-
benzoyl)-5-
methoxy-2-
methylindole-3-
acetoxyacetic
acid =
acemetacin

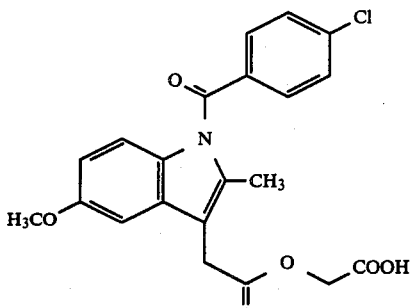

(Z)—5-Fluoro-
2-methyl-1-([(4-
methylsulphinyl)-
phenyl]-
methylene)-
1H—indene-3-
acetic acid

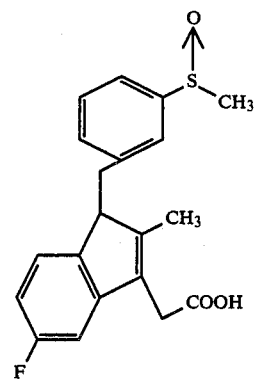

4-Butyl-1,2-
diphenyl-3,5-
pyrazolidine-
dione =
phenylbutazone

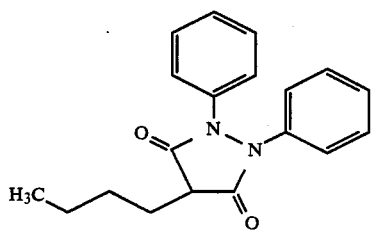

4-(3-Methyl-2-
butenyl)-1,2-
diphenylpy-
razolidine-3,5-
dione =
feprazone

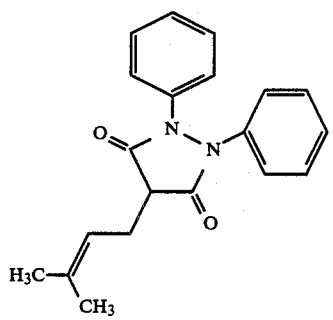

2-(4-Chloro-
phenyl)-
methyl-5-
benzoxazole-
acetic acid =
benoxaprofen

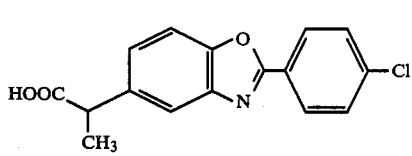

4-Hydroxy-2-
methyl-N—2-
thiazolyl-2H—
1,2-benzothia-
zine-3-carbox-
amide 1,1-
dioxide

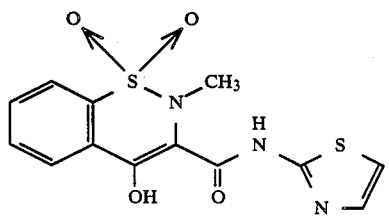

4-Hydroxy-2-
methyl-N—2-
pyridinyl-2H—
1,2-benzothia-
zine-3-carbox-
amide 1,1-
dioxide

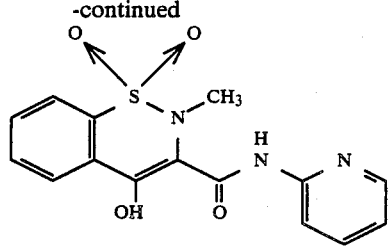

and their alkyl esters and substituted alkyl esters.

It is possible to incorporate in the plasters either one or several of the abovementioned antiinflammatory agents of the general formula I and II.

The antiinflammatory agents can be incorporated in the reservoir layer in an amount of 1–30% by weight, preferably 2–20% by weight. The % by weight indicated relates to the total reservoir.

These antiinflammatory agents can be mixed with other additional active substances or cooling or fragrance-releasing substances, preferably methyl salicylate, glycol salicylate, salicylic acid, menthol, peppermint oil, camphor, thymol, acrinol, scopolia extract, chlorpeniramine maleate, benzyl nicotinate, capsicum extract, nonylvanillylamide and capsaicin.

Where necessary, the plasters according to the invention can be mixed with additives and fillers, for example agents to protect from aging, antioxidants and strengthening fillers, as long as the gel-like properties are not destroyed.

Known systems for releasing active compounds, such as, for example, gels, ointment bases and plasters release about 0.5–20% of active compound in 7 hours. In contrast, the plasters according to the invention which are described above, release up to 70% of active compound in 7 hours, and the bioavailability is significantly greater (3–5 times greater). The systems according to the invention can be adjusted in respect of their rate of release of active compound virtually at will by changing the proportion of polymer, of the carrier and of the resin. The covering layer used for the plasters according to the invention is a simultaneous or consecutive course formation knit, which had longitudinal and transverse elasticity, (see, for example, Koch-Satlow, Grosses Textillexikon (Comprehensive Textile Lexicon), Deutsche Verlagsanstalt Stuttgart 1965). According to this, simultaneous and consecutive course formation knits are textile sheet-like structures which are produced from one or more thread systems by loop formation on machines for simultaneous or consecutive course formation. A distinction is made between two categories: simultaneous and consecutive course formation weft knits (main feature: threads run in the transverse directions, analogous to the direction of the weft in weaves) and warp knits (main feature: threads run in the longitudinal direction, analogous to the direction of the warp in weaves).

The terminological separation, which is customary in specialist terminology, into simultaneous and consecutive course formation knits relates to the process of production. In simultaneous course formation knitting, the loops of a course are formed (knocked off) simultaneously, while in consecutive course formation knitting one loop is produced after the other. However, there are exceptions to this in the assignment of terms. There is no structural difference between simultaneous and consecutive course formation weft knits.

In contrast to weaves, simultaneous and consecutive course formation knits have high extensibility and elasticity, especially in the lateral direction; moreover, as a consequence of the loop structure, they have a large pore volume, and this favours permeability to air and thermal insulation. These and other properties can be essentially modified by the structure and the selection of the textile fibre and yarn.

The simultaneous or consecutive course formation knits which are used according to the invention preferably have stretch characteristics. The methods customary in textile technology are used to achieve these stretch characteristics (see Koch-Satlow, page 441) or otherwise elastomeric fibres or elastomeric yarns are used immediately on selection of the basic materials for the simultaneous and consecutive course formation knits.

Apart from the simultaneous and consecutive course formation knits, it is generally possible to use as the covering layer for the plasters according to the invention textile sheet-like structures having stretch characteristics, that is to say all three-dimensional structures made of natural and synthetic textile fibres, such as braids, bonded webs or felts, are suitable as the covering layer. The basic material used for the covering layer is, inter alia, fibres and filaments made of nylon, polyester, polyurethane, nylon-polyurethane, cotton, viscose staple and animal wool.

The textile covering layer of the plasters according to the invention is impregnated or coated. The customary techniques and materials are used for coating and impregnation (see also Koch-Satlow, pages 157-159 and pages 616 et seq.).

The covering layer is preferably impregnated or coated with polyisobutylene. In this case, the molecular mass of the polyisobutylene is preferably greater than 1,000,000 g/mol (viscosity average).

The preferred coating and impregnation materials are the polyisobutylenes which are also contained in the reservoir layer but have higher molecular weights and no adhesiveness.

The protective detachable layer of the plasters according to the invention can be composed of occlusive, flexible or non-flexible materials, such as polyethylene, polypropylene, polyethylene terephthalate, nylon and similar known films. It is also possible to use as the detachable film metal foils, such as aluminum foil, alone or laminated with polymers. It is also possible to use multilayer foils, such as laminates of polyethylene with polyester/PE terephthlate and with vapour deposition of aluminum Other detachable foils are, inter alia, polyesters treated with silicone, polyethylene terephthalate with terminal silicone groups, treated paper, paper treated with silicone, paper coated with polyethylene and the like.

The invention also relates to a process for the production of medicinal plasters comprising a covering layer, a reservoir layer for active compound, and a detachable protective layer which is essentially impermeable to the active compounds, which process is characterized in that a polymer component containing polyisobutylene, one or more carriers and one or more resins are dissolved in a solvent, and 1 to 30% by weight of active compound is likewise dissolved in a solvent, these solutions are combined, the combined solutions are applied uniformly to a covering layer which is essentially impermeable to the active compounds and comprises a textile sheet-like structure, in particular a simultaneous or consecutive course formation knit, which is longitudinally and transversely elastic and is impregnated or coated with a polymer, and the covering layer is dried and, where appropriate, after drying is provided on the coated side with a detachable protective layer.

PREPARATION EXAMPLES

Example 1

A 12.5% strength polyisobutylene solution (M.W. viscosity average 1,270,000) (in petroleum) is applied to silicone-coated paper, and a simultaneous course formation knit consisting of nylon-polyurethane fibres is laminated on and dried in a drying channel stepwise at 70°/90°/110° C. (polymer 30 g/m$^2$).

A mixture dissolved in petroleum/acetone and composed of 36.000 g of polyisobutylene M.W. viscosity average 400,000,
44.928 g of low-viscosity paraffin,
9.000 g of polyterpene resin from β-pinene,
10.000 g of etofenamate and
0.072 g of agent to protect from aging
is applied to silicone-coated paper and dried in a drying channel stepwise at 70°/90°/100° C. (system for releasing active compound about 150 g/m$^2$).

After drying, the simultaneour course formation knit impregnated with polyisobutylene and having stretch characteristics was laminated on to the silicone coated paper containing the components initially dissolved in the petroleum/acetone.

Example 2

A polymer solution (petroleum/acetone) consisting of 36.000 g of polyisobutylene M.W. viscosity average 1,270,000,
44.928 g of low-viscosity paraffin,
9.000 g of polyterpene resin from α-pinene,
10.000 g of etofenamate and
0.072 g of agent to protect from aging
was applied to silicone-coated paper and dried in a drying channel stepwise at 70°/90°/110° C.

After drying, the system, with polyisobutylene, for release of active compound (as in Example 1) was laminated onto coated strecht material so that the active compound was sandwiched between the stretch material and the silicone-coated paper.

The absorption of the active compounds from plasters according to the invention is as good as that from conventional plasters coated with aluminium/polyethylene foils.

The methods and materials used for laminating the active compound depot onto the textile sheet-like structures having stretch characteristics are, inter alia, those described in Koch-Satlow, Grosses Textillexikon.

What is claimed is:

1. A medicinal plaster comprising a covering layer, a reservoir layer for an active compound and a detachable protective layer which is substantially impermeable to the active compound, said reservoir layer containing 1 to 30% by weight of an active compound and an elastomer comprising a polyisobutylene polymer, a carrier and a resin, said covering layer being substantially impermeable to said active compound and comprising a textile sheet-like structure which is longitudinally and transversely elastic and is impregnated or coated with a polymer.

2. A medicinal plaster according to claim 1 wherein said resin is an adhesion-conferring resin.

3. A medicinal plaster according to claim 2 wherein said carrier is a polybutadiene oil, liquid paraffin or mixture thereof.

4. A medicinal plaster according to claim 3 wherein said covering layer is impregnated with a polymer.

5. A medicinal plaster according to claim 3 wherein said covering layer is coated with a polymer.

6. A medicinal plaster according to claim 1 wherein said polyisobutylene polymer is one having a molecular mass distribution $M_w/M_n$ of 1.5 to 3.5 and a viscosity average of molecular mass of 30,000 to 4,000,000, said active compound is an antiinflammatory agent and said covering layer consists essentially of a textile sheet-like structure which is impermeable to said active compound, is longitudinally and transversely elastic, and is impregnated or coated with a polymer.

7. A medicinal plaster according to claim 6 wherein said molecular mass distribution $M_w/M_n$ is 2.0 to 3.0.

8. A medicinal plaster according to claim 6 wherein said polyisobutylene polymer is a polyisobutylene homopolymer.

9. A medicinal plaster according to claim 6 wherein said polyisobutylene polymer is a polyisobutylene copolymer with 1 to 5 mol percent of a conjugated diene.

10. A medicinal plaster according to claim 1 wherein said reservoir contains 30 to 60% by weight of polyisobutylene polymer, 30 to 60% by weight of carrier and 2 to 40% by weight of resin in addition to said active compound.

11. A medicinal plaster according to claim 1 wherein said polyisobutylene has a viscosity average of molecular mass of 50,000 to 1,000,000 g/mol.

12. A medicinal plaster according to claim 1 wherein said polyisobutylene is one of a viscosity average of molecular weight of 80,000 to 500,000 g/mol.

13. A medicinal plaster according to claim 9 wherein said diolefin is a $C_4-C_6$ diene.

14. A medicinal plaster according to claim 1 wherein said covering layer contains polyisobutylene having a viscosity average of molecular mass greater then 1,000,000 g/mol.

15. A medicinal plaster according to claim 1 wherein said active compound is an antiinflammatory agent of the formula

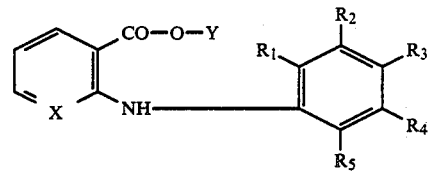

wherein
$R_1-R_5$ can be identical or different, and denote hydrogen, halogen, lower alkyl or substituted alkyl,
X denotes N or CH and
Y denotes hydrogen, metal ions, alkyl or substituted alkyl,
and/or of the formula II

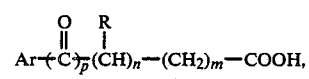

in which
R denotes hydrogen, lower alkyl or substituted alkyl,
Ar denotes aryl, heteroaryl, substituted aryl or substituted heteroaryl, and
n+m denote an integer, and have the value zero, 1 or 2, and
p denotes zero or 1,
with the proviso that AR does not denote aryl or heteroaryl when n and m and p have the value zero.

16. A medicinal plaster according to claim 1 wherein said active compound is etofenamate.

17. A medicinal plaster according to claim 1 wherein said carrier comprises liquid paraffin.

18. A medicinal plaster according to claim 17 wherein said resin comprises polyterpene resin from a pinene.

19. A medicinal plaster according to claim 18 wherein said detachable protective layer comprises silicone treated paper.

20. A medicinal plaster according to claim 1, wherein the textile sheet-like structure is a simultaneous or consecutive course formation knit.

21. A medicinal plaster according to claim 20, wherein the knit is selected from the group consisting of weft knits and warp knits.

22. A process for the production of a medicinal plaster comprising a covering layer, reservoir layer for active compound and a detachable protective layer which is substantially impermeable to said active compound which comprises:

A. dissolving a polybutylene polymer, a carrier and a resin in a solvent;
B. dissolving 1 to 30% by weight of active compound in a second solvent;
C. combining the solvents of steps A and B and applying the same uniformly to a covering layer which is substantially impermeable to said active compound and comprises a textile sheet-like structure which is longitudinally and transversely elastic and is impregnated or coated with a polymer;
D. drying said covering layer; and
E. thereafter disposing over the so dried material a detachable protective layer.

* * * * *